(12) United States Patent
Yakuphanoglu et al.

(10) Patent No.: US 10,571,085 B2
(45) Date of Patent: Feb. 25, 2020

(54) SOLAR SIMULATOR FILTER AND A METHOD OF FABRICATING THEREOF

(71) Applicant: King Abdulaziz University, Jeddah (SA)

(72) Inventors: Fahrettin Yakuphanoglu, Jeddah (SA); Ahmed A. Al-Ghamdi, Jeddah (SA)

(73) Assignee: King Abdulaziz University, Jeddah (SA)

( * ) Notice: Subject to any disclaimer, the term of this patent is extended or adjusted under 35 U.S.C. 154(b) by 167 days.

(21) Appl. No.: 15/672,990

(22) Filed: Aug. 9, 2017

(65) Prior Publication Data
US 2019/0049078 A1   Feb. 14, 2019

(51) Int. Cl.
| | |
|---|---|
| F21S 8/00 | (2006.01) |
| G01N 21/25 | (2006.01) |
| H01L 31/18 | (2006.01) |
| H02S 50/10 | (2014.01) |
| G01J 1/08 | (2006.01) |
| G01J 1/04 | (2006.01) |
| H02S 50/15 | (2014.01) |
| G02B 5/20 | (2006.01) |

(52) U.S. Cl.
CPC ............. *F21S 8/006* (2013.01); *G01J 1/0488* (2013.01); *G01J 1/08* (2013.01); *G01N 21/255* (2013.01); *G02B 5/20* (2013.01); *H01L 31/18* (2013.01); *H02S 50/10* (2014.12); *H02S 50/15* (2014.12)

(58) Field of Classification Search
CPC .......... F21S 8/006; G01N 21/255; G01J 1/08; G01J 1/0488; H02S 50/10; H01L 31/18
See application file for complete search history.

(56) References Cited

U.S. PATENT DOCUMENTS 4,125,775 A * 11/1978 Chodak ............... F21V 9/02
                                                        250/504 R
2009/0297838 A1   12/2009 Knapp

FOREIGN PATENT DOCUMENTS

| CN | 103050289 A | 4/2013 |
|---|---|---|
| EP | 0 510 919 A1 | 10/1992 |
| WO | 88/01230 A1 | 2/1988 |
| WO | 2009/053236 A1 | 4/2009 |
| WO | 2014/200183 A1 | 12/2014 |

OTHER PUBLICATIONS

Xiaoming Huang, Zhexun Yu, Shuqing Huang, Quanxin Zhang, Dongmei Li, Yanhong Luo, Qingbo Meng, Preparation of fluorine-doped tin oxide (SnO2:F) film on polyethylene terephthalate (PET) substrate, Materials Letters 64 (2010) 1701-1703. (Year: 2010).*

(Continued)

*Primary Examiner* — Bijan Ahvazi
(74) *Attorney, Agent, or Firm* — Oblon, McClelland, Maire & Neustadt, L.L.P.

(57) ABSTRACT

A solar simulator filter that includes a flexible substrate and one or more layers of oxide materials, e.g. fluorine-doped tin oxide and indium-doped tin oxide, wherein a thickness of said layers is no more than 500 nm, and wherein the solar simulator filter generates a spectral output that closely matches a solar irradiance spectrum. Various embodiments of the solar simulator filter and a method of fabricating thereof is described.

10 Claims, 5 Drawing Sheets

(56) References Cited

OTHER PUBLICATIONS

R. Riveros, E. Romero, and G. Gordillo, Synthesis and Characterization of Highly Transparent and Conductive SnO2:F and In2O3:Sn thin Films Deposited by Spray Pyrolysis, Brazilian Journal of Physics, vol. 36, No. 3B, Sep. 2006. (Year: 2006).*

E. Elangovan, K. Ramamurthi, Optoelectronic Properties of Spray Deposited SnO2:F Thin Films for Window Materials in Solar Cells, Journal of Optoelectronics and Advanced Materials vol. 5, No. 1, Mar. 2003, p. 45-54. (Year: 2003).*

M. K. M. Ali, K. Ibrahim1, M.Z. Pakhuruddin, and M. G. Faraj, Optical and Electrical Properties of Indium Tin Oxide (ITO) Thin Films Prepared by Thermal Evaporation Method on Polyethylene Terephthalate (PET) Substrate, Advanced Materials Research, vol. 545, pp. 393-398, 2012. (Year: 2012).*

Sigma-Aldrich, "Indium Tin Oxide Coated PET", URL: http://www.sigmaaldrich.com/catalog/product/aldrich/639303?lang=en&region=US, 1 Page total, (2017).

MG Super Labs India, "ITO (Indium Tin Oxide) Coated PET Plastic—100mm x 200mm", The E-Store @ MG Super Labs, 2 Pages total, (2017).

MTI Corporation, "ITO Coated Plastic PET Film, 0.175mm Thick x 300mm Width x 1 Meter Length, 14 ohm/sq, ITO Layer: 115nm+/−10mn", URL: http://www.mtixll.com/ITO-Film.aspx, 1 Page total, (2017).

Xiao, Y.M., et al., "Low Temperature Fabrication of High Performance and Transparent Pt Counter Electrodes for Use in Flexible Dye-Sensitized Solar Cells", Chinese Science Bulletin, vol. 57, No. 18, pp. 2329-2334, (Jun. 2012).

Pandey, A.K., et al., "Efficient Flexible and Thermally Stable Pentacene/C60 Small Molecule based Organic Solar Cells", Applied Physics Letters, vol. 89, Issue 21, 1 Page total, (Nov. 2006) (Abstract only).

ASTM International, "Standard Specification for Solar Simulation for Photovoltaic Testing", 5 Pages total, (May 2005).

Emery, K.A., "Solar Simulators and I-V Measurement Methods", Solar Cells, vol. 18, No. 3-4, pp. 251-260, (1986).

Paulescu, M., et al., "Chapter 2—Solar Radiation Measurements", Weather Modeling and Forecasting of PV Systems Operation, pp. 17-42, (2013).

* cited by examiner

SOLAR SIMULATOR FILTER AND A METHOD OF FABRICATING THEREOF

BACKGROUND OF THE INVENTION

Technical Field

The present invention relates to a solar simulator filter that includes a flexible substrate, and one or more layers of oxide materials, such as fluorine-doped tin oxide and indium-doped tin oxide, with a thickness of no more than 500 nm.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Solar simulators are used to generate an irradiance spectrum that closely matches a solar irradiance spectrum for various purposes e.g. testing photovoltaic modules. Therefore, one requirement of a solar simulator is that it must generate an optical output spectrum that closely matches that of natural sunlight. Standards defining an acceptable spectral output for solar simulators have been developed by both ASTM International and the IEC.

To generate acceptable spectral output for solar simulators, solar simulator filters can be used to attenuate the output in a wide wavelength range from infrared wavelengths to ultraviolet wavelengths, e.g. from 300 nm to 2,500 nm. The solar simulator filters are generally exposed to a continuous, a flashed, or a pulsed light source, such as a xenon arc lamp, a metal halide lamp, a halogen lamp, or a combination thereof. The xenon arc lamp is the most common lamp used in solar simulators and it emits radiation of higher than 700 nm. This excess radiation can be compensated using a solar simulator filter to attenuate the output in the near infrared.

In view of the forgoing, one objective of the present invention is to provide a solar simulator filter that includes a flexible substrate and one or more layers of oxide materials such as fluorine-doped tin oxide and indium-doped tin oxide, wherein a thickness of said layers is no more than 500 nm. The solar simulator filter is shown to generate an irradiance spectrum that closely matches a solar irradiance spectrum when disposed across from a light source. Another objective of the present invention relates to a method of fabricating the solar simulator filter.

BRIEF SUMMARY OF THE INVENTION

According to a first aspect, the present disclosure relates to a solar simulator filter, including i) a flexible substrate, ii) an oxide material disposed on the flexible substrate, wherein the oxide material comprises fluorine-doped tin oxide, and wherein the solar simulator filter transmits light having an irradiance in the range of 1.0 to 1.6 $W/m^2/nm$ in the wavelength range of 300 to 750 nm, an irradiance in the range of 0.4 to 1.0 $W/m^2/nm$ in the wavelength range of 750 to 1,400 nm, and an irradiance in the range of 0.1 to 0.4 $W/m^2/nm$ in the wavelength range of 1,400 to 2,500 nm.

In one embodiment, the oxide material further comprises an oxide of a post-transition metal selected from the groups 13 to 15 of the periodic table.

In one embodiment, the oxide of the post-transition metal is indium oxide, tin oxide, and/or indium-doped tin oxide.

In one embodiment, the flexible substrate has a transmittance of at least 60% at a wavelength in the range of 300 to 2,500 nm.

In one embodiment, the flexible substrate is a thermoplastic polymer selected from the group consisting of polyethylene terephthalate, polyethylene, polypropylene, and polyvinyl chloride.

In one embodiment, an average particle size of the fluorine-doped tin oxide is in the range of 1 to 100 nm.

In one embodiment, an amount of fluorine in the fluorine-doped tin oxide is in the range of 0.1 to 5 wt %, relative to the total weight of the fluorine-doped tin oxide.

In one embodiment, the oxide material further comprises indium-doped tin oxide, and wherein an amount of indium in the indium-doped tin oxide is in the range of 8 to 10 wt %, relative to the total weight of the indium-doped tin oxide.

In one embodiment, the oxide material disposed on the flexible substrate is in a form of a layer with a thickness of 50 to 200 nm.

In one embodiment, the flexible substrate has a thickness in the range of 50 μm to 5 mm.

In one embodiment, the solar simulator filter has a surface resistivity in the range of 5 to 60 Ω/sq.

According to a second aspect, the present disclosure relates to a solar simulator device, including i) at least one light source with a power output in the range of 0.1 to 1.5 $W/m^2/nm$, ii) the solar simulator filter disposed within a distance in the range of 0.1 to 5 m from said light source, wherein at least a portion of light provided by said light source is configured to transmit through the solar simulator filter.

According to a third aspect, the present disclosure relates to a method of fabricating the solar simulator filter, involving i) mixing a fluorine-containing compound with water and a first amount of a dihydroxyalkane to form a fluorine-containing solution, ii) separately mixing a tin-containing compound with water and a second amount of the dihydroxyalkane to form a tin-containing solution, iii) mixing the fluorine-containing solution with the tin-containing solution and an alkanolamine to form a spin-coating precursor, iv) spin-coating the spin-coating precursor on the flexible substrate to form the solar simulator filter.

In one embodiment, the method further involves i) separately mixing an indium-containing compound with water and a third amount of the dihydroxyalkane to form an indium-containing solution, ii) mixing the indium-containing solution with the spin-coating precursor prior to the spin-coating.

In one embodiment, the spin-coating precursor is spin-coated at a centrifugal speed of 2400 to 3600 rpm for a period of 10 to 60 seconds.

In one embodiment, the dihydroxyalkane is ethylene glycol.

In one embodiment, the fluorine-containing compound is ammonium fluoride or a fluoride compound of an alkali metal or an alkaline earth metal, the tin-containing compound is a tin nitrate, a tin acetate, a tin sulfate, or a hydrate thereof, and the indium-containing compound is indium nitrate, indium acetate, indium sulfate, or a hydrate thereof.

In one embodiment, the fluorine-containing compound is ammonium fluoride, the tin-containing compound is tin acetate, and the indium-containing compound is indium nitrate.

In one embodiment, the alkanolamine is triethanolamine, and the spin-coating precursor has a pH in the range of 2 to 5.

In one embodiment, the method further involves i) drying the solar simulator filter, ii) repeating the spin-coating and the drying until a thickness of the fluorine-doped tin oxide disposed on the flexible substrate gets a value in the range of 200 to 500 nm.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1A:
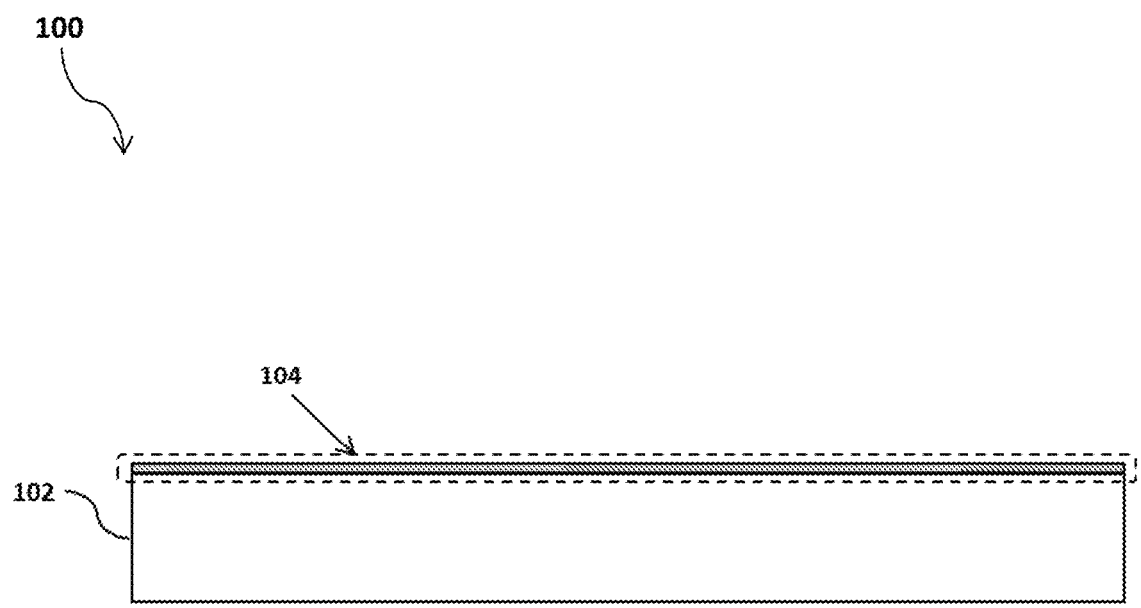
FIG. 1A is a cross-sectional view of a solar simulator filter having a layer of oxide materials.

Referring now to the drawings, wherein like reference numerals designate identical or corresponding parts throughout the several views.

Figure 1B:
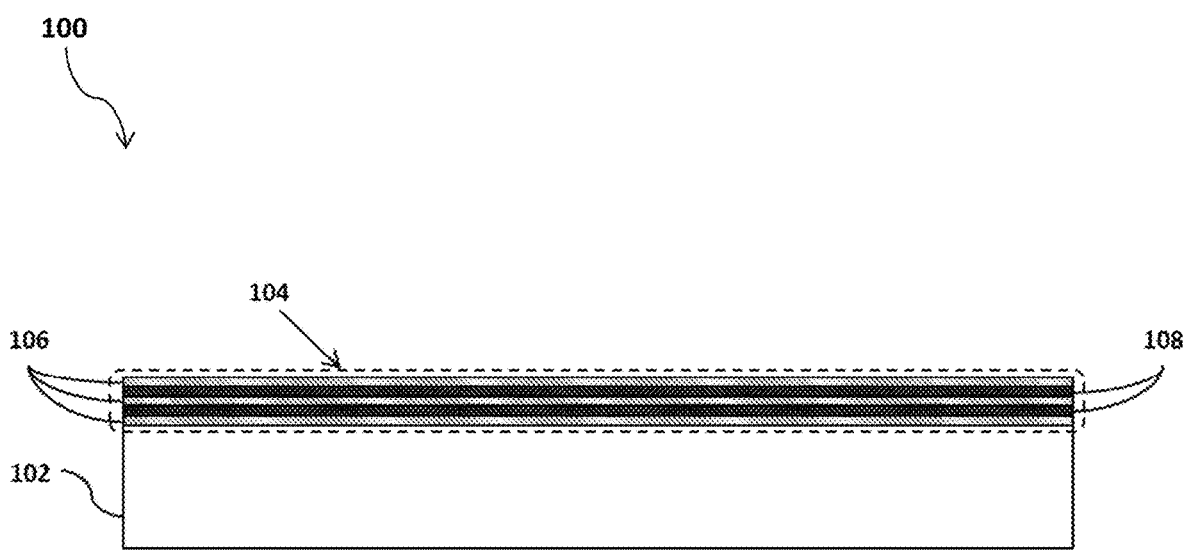
FIG. 1B is a cross-sectional view of a solar simulator filter having multiple layers of oxide materials, including one or more layers of fluorine-doped tin oxide and one or more layers of indium-doped tin oxide.

According to a first aspect, the present disclosure relates to a solar simulator filter 100. FIGS. 1A and 1B show a cross-sectional view of the solar simulator filter 100. As shown in these figures, the solar simulator filter 100 includes a flexible substrate 102 and one or more oxide materials 104 disposed thereon.

Referring again to FIGS. 1A and 1B, the one or more oxide materials 104 may be in the form of a layer, as shown in FIG. 1A, or a plurality of layers, as shown in FIG. 1B, that cover at least a portion of the flexible substrate 102. For example, in one embodiment, the layer covers at least 80%, preferably at least 85%, preferably at least 90%, preferably at least 95%, more preferably at least 99% of a surface area of the flexible substrate. Said layer or layers of oxide materials 104 may be disposed on the flexible substrate using a technique known in the art. For example, in one embodiment, said layer or layers of oxide materials may be disposed on the flexible substrate using spin-coating, plasma-enhanced sputtering, ion plate coating, physical vapor deposition, magnetron sputtering, ion beam sputtering, ion-assisted electron beam deposition, and the like, as known in the art.

In one embodiment, multiple layers of one or more oxide materials are disposed on the flexible substrate 102, thus forming a multi-layered solar simulator filter 100 (as shown in FIG. 1B). The stacking configuration and total thickness of the multi-layered solar simulator filter may vary depending on a desired transmittance spectrum. For example, in one embodiment, the multi-layered solar simulator filter includes oxide material A and oxide material B, with a stacking configuration of A-B-A, A-A-B, B-A-B, or B-B-A, wherein a total thickness of the multi-layered solar simulator filter is in the range of 200 to 500 nm, preferably 300 to 480 nm, preferably 400 to 450 nm. Accordingly, each layer of said oxide materials has a thickness of 50 to 200 nm, preferably 100 to 160 nm, preferably 130 to 150 nm. The multi-layered solar simulator filter may include at least 2 but no more than 10, preferably at least 3 but no more than 5 layers of the oxide materials.

In one embodiment, a shape and a geometry of the solar simulator filter 100 are substantially the same as a shape and a geometry of the flexible substrate 102. Since the flexible substrate can be manufactured or re-shaped into a variety of shapes and geometries, the solar simulator filter may also take a variety of shapes and geometries. Preferably the solar simulator filter 100 has a slab geometry with a thickness of 50 μm to 5 mm, preferably 500 μm to 4 mm, preferably 1 to 3 mm. Alternatively, the solar simulator filter 100 may have a curved geometry, e.g. a curved slab or a hemisphere, etc.

Preferably, in one embodiment, the solar simulator filter has a surface resistivity in the range of 5 to 60 Ω/sq, preferably 10 to 55 Ω/sq, preferably 20 to 50 Ω/sq.

In one embodiment, the flexible substrate 102 of the solar simulator filter 100 is a thermoplastic polymer selected from the group consisting of polyethylene terephthalate, polyethylene, polypropylene, and polyvinyl chloride. Preferably, the flexible substrate 102 may have a thickness in the range of 50 μm to 5 mm, preferably 500 μm to 4 mm, preferably 1 to 3 mm; and a transmittance of at least 60%, preferably at least 70%, preferably at least 80% at a wavelength in the range of 300 to 2,500 nm. In a preferred embodiment, the flexible substrate is polyethylene terephthalate with a thickness in the range of 50 μm to 5 mm, preferably 500 μm to 4 mm, preferably 1 to 3 mm. In a preferred embodiment, the absorption characteristics of a flexible substrate made from polyethylene terephthalate remain unchanged despite prolonged exposure to light. In a preferred embodiment, the solar simulator filter of this disclosure is flexible, and thereby a rigid substrate such as a glass substrate is preferably not used in the structure of the solar simulator filter. Alternatively, in certain applications, rigid substrates (e.g. glass substrates) may be utilized in lieu of or in addition to the flexible substrate and the solar simulator filter can still function as intended. The term "substrate" does not refer to a frame that supports the solar simulator filter and/or affixes the solar simulator filter in place. In fact, such frames may be rigid.

In one embodiment, the flexible substrate has a flexural modulus in the range of 1 to 50 MPa, preferably 5 to 40 MPa, preferably 8 to 30 MPa, preferably 10 to 25 MPa, and a flexural strength in the range of 0.5 to 20 MPa, preferably 1 to 15 MPa, preferably 4 to 12 MPa, preferably 6 to 10 MPa. The term "flexible" as used herein preferably refers to a bendable substrate that can bend up to certain strain values in flexural mode, for example, up to 10%, preferably up to 15%, but no more than 20%, in accordance with the ASTM D790.

The oxide material disposed on the flexible substrate 102 preferably includes fluorine-doped tin oxide (FTO) 106. In one embodiment, an amount of fluorine in the fluorine-doped tin oxide 106 is in the range of 0.1 to 5 wt %, preferably 0.5 to 4.5 wt %, preferably 1 to 4 wt %, preferably 1.5 to 3.5 wt %, relative to the total weight of the fluorine-doped tin oxide. Also, a tin-to-oxygen molar ratio in the FTO is 1:1.5 to 1:2.5, preferably 1:1.8 to 1:2.2.

In one embodiment, the FTO 106 is in a form of particulates with an average particle size in the range of 1 to 100 nm, preferably 10 to 95 nm, preferably 50 to 90 nm. In a preferred embodiment, the FTO 106 as disclosed herein consists of fluorine, tin, and oxygen. Accordingly, other elements, such as chlorine, are preferably not present in the composition of the FTO.

In some embodiments, the solar simulator filter 100 includes a flexible substrate 102 and a layer of the FTO 106 disposed thereon. Said layer of the FTO 106 may preferably provide a transmittance of at least 85%, preferably at least 90%, in the visible light region, i.e. at a wavelength of 400 to 700 nm. Furthermore, said layer may provide an infrared shielding property, i.e. having an infrared transmittance of 40% or less, more preferably 30% or less, at a wavelength of 1500 nm and above, and an infrared transmittance of 25% or less, more preferably 20% or less, a wavelength of 2000 nm and above. Preferably, the presence of tin in the FTO may affect the aforementioned transmittance behavior of the solar simulator filter. In view of that, the amount of tin present in the FTO is in the range of 10 to 80 wt %, preferably 20 to 70 wt %, preferably 30 to 60 wt %, relative to the total weight of the FTO.

In addition to the FTO, the solar simulator filter 100 may further include an oxide of a post-transition metal selected from the groups 13 to 15 of the periodic table. In a preferred embodiment, a layer or layers of indium oxide, tin oxide, or indium-doped tin oxide are separately disposed adjacent to the FTO. The phrase "separately disposed adjacent to the FTO" as used herein refers to embodiments wherein the layer or layers that contain indium oxide, tin oxide, or indium-doped tin oxide have distinct boundaries when disposed adjacent to the layer of the FTO 106, i.e. there is a distinct interface between the indium oxide, tin oxide, or indium-doped tin oxide layers and the FTO layers.

In a preferred embodiment, the oxide material includes indium-doped tin oxide (ITO) 108, wherein an amount of indium in the ITO 108 is in the range of 8 to 10 wt %, preferably 8.5 to 9.5 wt %, preferably about 9 wt %, relative to the total weight of the indium-doped tin oxide.

In another preferred embodiment, the solar simulator filter 100 includes a layer of the FTO and a layer of the ITO disposed onto the flexible substrate 102. Accordingly, in one embodiment, the layer of the FTO is disposed onto the flexible substrate, and the layer of the ITO is disposed onto the layer of the FTO. Alternatively, the layer of the ITO may be disposed onto the flexible substrate, and the layer of the FTO is disposed onto the layer of the ITO.

In another preferred embodiment, the solar simulator filter 100 includes multiple alternating layers, preferably at least 2 but no more than 10, or preferably at least 3 but no more than 5 of the fluorine-doped tin oxide 106 and the indium-doped tin oxide 108, wherein each layer has a thickness of 50 to 200 nm, preferably 100 to 160 nm, preferably 130 to 150 nm.

Figure 2:
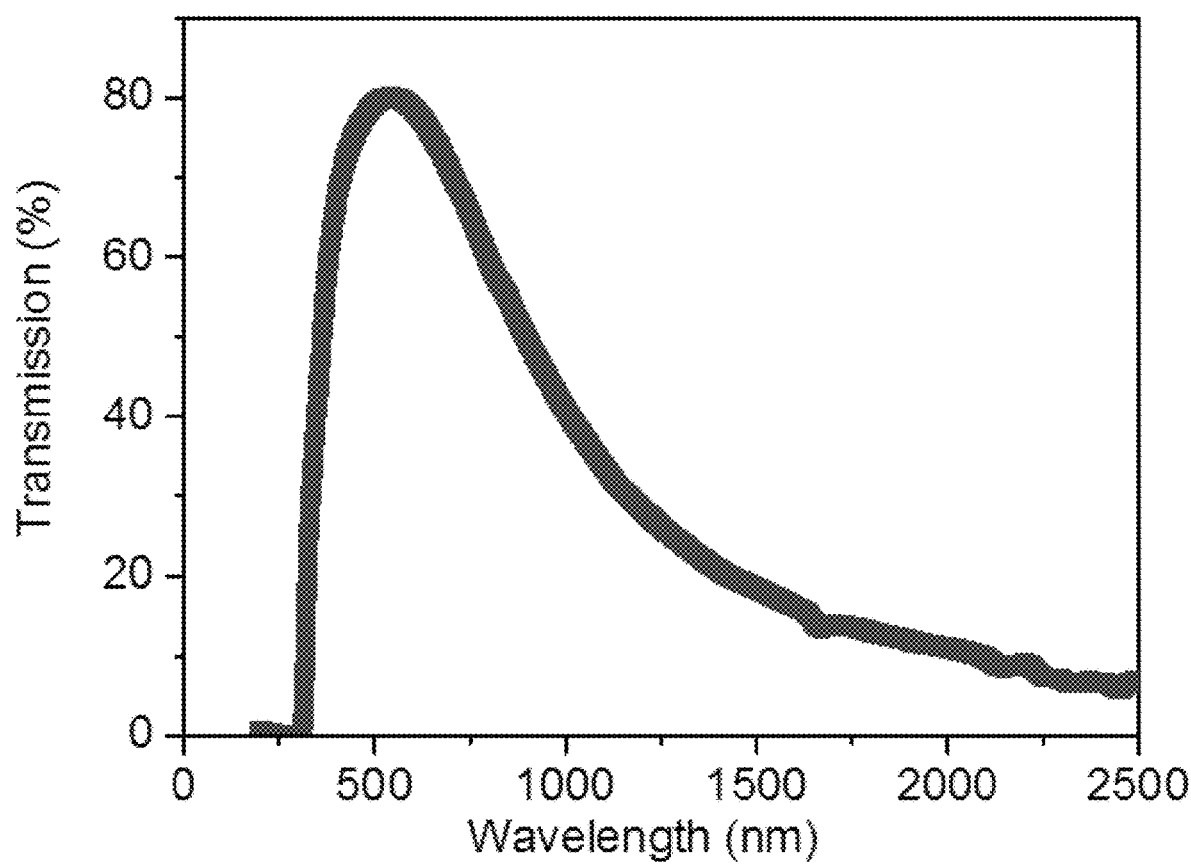
FIG. 2 represents a transmittance spectrum of a solar simulator filter having a layer of indium-doped tin oxide (ITO).

FIG. 2 is a representative transmittance characteristics of the solar simulator filter 100 having a layer of the ITO disposed onto the flexible substrate. Also, a solar simulator filter having a layer of the FTO and a layer of the ITO disposed onto the flexible substrate may provide substantially the same transmittance characteristics as shown in FIG. 2.

Accordingly, in a preferred embodiment, the solar simulator filter 100 provides a maximum transmittance of no more than 90%, preferably no more than 85%, preferably no more than 80% at a wavelength in the range of 500 to 600 nm, which is in compliance with the IEC 60904-9 standards. The solar simulator filter 100 further provides a transmittance of 40% or less, preferably 35% or less at a wavelength in the range of 900 to 1100 nm, an infrared transmittance of 25% or less, more preferably 20% or less, at a wavelength of 1500 nm and above, and an infrared transmittance of 20% or less, more preferably 15% or less, a wavelength of 2000 nm and above, and a zero transmittance at a wavelength of below 300 nm.

Preferably, the solar simulator filter 100, which has the aforementioned transmittance characteristics, transmits light having an irradiance in the range of 1.0 to 1.6 $W/m^2/nm$, preferably 1.1 to 1.55 $W/m^2/nm$, preferably 1.2 to 1.5 $W/m^2/nm$, in the wavelength range of 300 to 750 nm, preferably 330 to 740 nm; an irradiance in the range of 0.4 to 1.0 $W/m^2/nm$, preferably 0.45 to 0.95 $W/m^2/nm$, preferably 0.5 to 0.9 $W/m^2/nm$, in the wavelength range of 750 to 1,400 nm, preferably 780 to 1,300 nm; and an irradiance in the range of 0.1 to 0.4 $W/m^2/nm$, preferably 0.15 to 0.35 $W/m^2/nm$, preferably 0.2 to 0.3 $W/m^2/nm$, in the wavelength range of 1,400 to 2,500 nm, preferably 1,500 to 2,400 nm.

In another embodiment, a transmittance of the solar simulator filter at the visible light wavelength is reduced by at least 10%, preferably at least 20%, but no more than 30%, relative to the initial transmittance of the solar simulator filter at the visible light wavelength, when the thickness of the oxide materials is increased by no more than 20%, preferably no more than 40%, relative to the initial thickness of the oxide materials.

In one embodiment, the flexible substrate has a relatively large resistance in the range of 1 MΩ to 10 MΩ, preferably 2 MΩ to 8 MΩ, preferably 3 MΩ to 6 MΩ, and thus the solar simulator filter cannot be utilized in a solar cell, particularly a dye-sensitized solar-cell, and related applications.

Figure 1C:
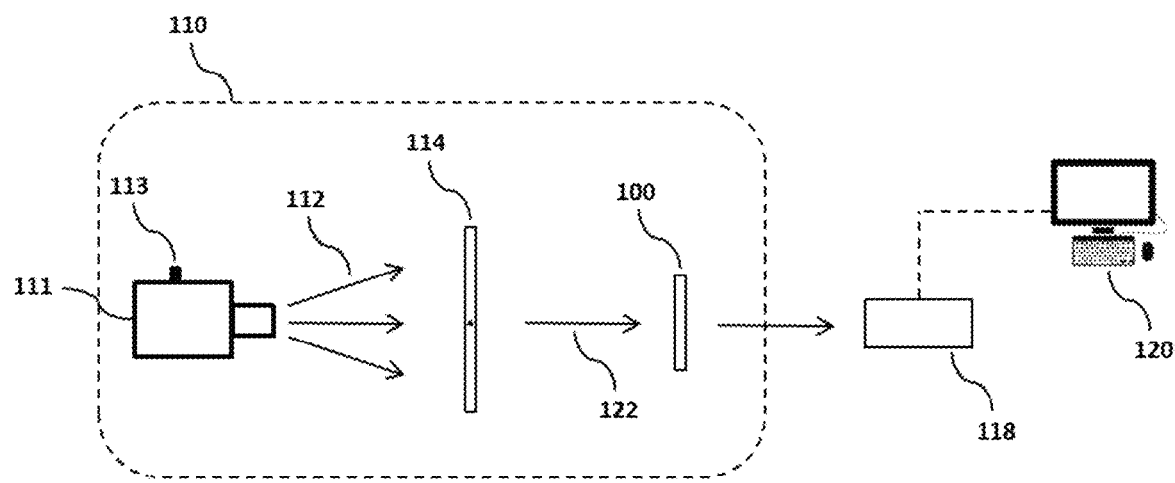
FIG. 1C is a schematic representation of a solar simulator device.

According to a second aspect, the present disclosure relates to a solar simulator device 110 that includes one or more light sources 111 and the solar simulator filter 100 disposed within a distance in the range of 0.1 to 5 m, preferably 0.2 to 4 m, preferably 0.3 to 3 m, preferably 0.4 to 2 m, preferably 0.5 to 1 m, from said light source, as shown in FIG. 1C. In an alternative embodiment, the solar simulator filter may be directly adjacent to the light source (not shown). Accordingly, the solar simulator filter transmits at least a portion of light 112 provided by the one or more light sources 111, and the transmitted light has an irradiance spectrum that closely matches a solar irradiance spectrum.

Figure 3:
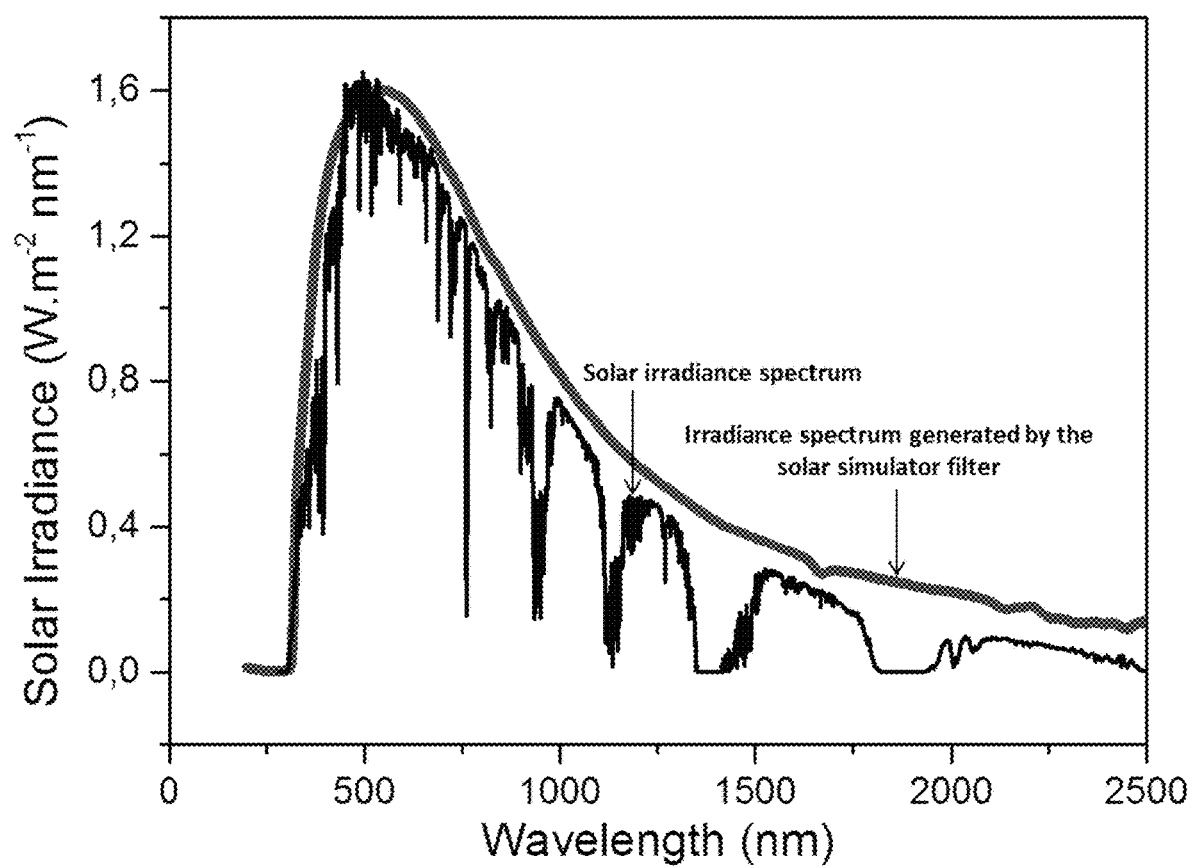
FIG. 3 represents a solar irradiance spectrum and an irradiance spectrum transmitted through a solar simulator filter having a layer of indium-doped tin oxide (ITO).

Referring now to FIG. 1C, in one embodiment of the solar simulator device 110, light 112 provided by the light source 111 is first passed through an optional aperture 114, and an incident beam 122 is further passed through the solar simulator filter 100, and a transmitted light with a desired irradiance spectrum is obtained. The transmitted light may further be collected by a detector 118, and the irradiance spectrum of the transmitted light may be compared with the solar irradiance spectrum using a computer 120. The results are shown in FIG. 3.

In some embodiments, an intensity of the light 112 produced by the light source 111 is governed by a light source controller (e.g. a power supply), which can be controlled by the computer 120. The light 112 may be turned 'on' or 'off' using a shutter 113 located on the light source 111. The shutter 113 may be an electric switch that is controlled by the computer 120. In another embodiment, a position of each of the aperture 114 and the solar simulator filter 100 can vary relative to the light source 111. Preferably, a ratio of a distance between the light source 111 and the aperture 114 to the distance between the light source 111 and the solar simulator filter 100 is in the range of 0.05:1 to 0.5:1, preferably 0.1:1 to 0.4:1, preferably 0.15:1 to 0.35:1. The aperture 114 may include a circular hole with a diameter of no more than 1 mm, preferably no more than 0.5 mm. Alternatively, the aperture may include a slit, i.e. a long and narrow opening, with a width of no more than 0.5 mm, preferably no more than 0.1 mm, and a length in the range of 1 to 10 cm, preferably 2 to 8 cm, preferably 4 to 6 cm.

The term "light source" as used herein refers to devices that provide light in a desired wavelength, e.g. microwave radiation, infrared radiation, visible light radiation, ultraviolet radiation, X-ray radiation, gamma radiation, etc. Exemplary light sources that can be utilized include, but are not limited to a xenon arc lamp, a high-intensity discharge (HID) lamp, a mercury vapor lamp, a metal halide lamp, a ceramic metal halide lamp, a sodium vapor lamp, a halogen lamp, and a quartz tungsten halogen lamp. Preferably, the light source is selected in accordance with a power output requirement. For example, to receive a power output equivalent to that of solar irradiance, i.e. about 1.05 $W/m^2/nm$ in the visible light wavelength range of 400 to 700 nm, one or more xenon arc lamps may be utilized. In one embodiment, the light source provides light in a spectrum with a wavelength range of 100 to 5,000 nm, preferably 200 to 4,000 nm, preferably 250 to 3,000 nm, preferably 300 to 2,500 nm, wherein a power output of said light source is in the range of 0.1 to 1.5 $W/m^2/nm$, preferably 0.5 to 1.4 $W/m^2/nm$, preferably 0.8 to 1.3 $W/m^2/nm$, preferably 0.9 to 1.2 $W/m^2/nm$, preferably 1.0 to 1.1 $W/m^2/nm$. The xenon flash lamp 10 in this embodiment is a common long xenon lamp of a straight tube type capable of generating a flash light having a light-emitting pulse width of the order of about 5 to 100 milliseconds, for example.

Due to the presence of the one or more oxide materials 104 disposed on the flexible substrate 102, when the solar simulator filter 100 is disposed across from the light provided by such light sources having a power output in the range of 0.1 to 1.5 $W/m^2/nm$, preferably 0.5 to 1.4 $W/m^2/nm$, preferably 0.8 to 1.3 $W/m^2/nm$, preferably 0.9 to 1.2 $W/m^2/nm$, preferably 1.0 to 1.1 $W/m^2/nm$, a transmitted light is generated having an irradiance spectrum that closely matches a solar irradiance spectrum at a wavelength range of 300 to 2,500 nm. FIG. 3 shows an irradiance spectrum of a light transmitted through the solar simulator filter versus a solar irradiance spectrum.

In general, the term "disposed across" as used in this disclosure refers to an orientation where a first object is located within a distance in the range of 0.1 to 5 m, preferably 0.2 to 4 m, preferably 0.3 to 3 m, preferably 0.4 to 2 m, preferably 0.5 to 1 m from a second object. For example, the phrase "the solar simulator filter disposed across from the light source" refers to an orientation where the solar simulator filter is located within a distance in the range of 0.1 to 5 m, preferably 0.2 to 4 m, preferably 0.3 to 3 m, preferably 0.4 to 2 m, preferably 0.5 to 1 m, from the light source, as shown in FIG. 1C. Accordingly, at least a portion of light provided by the light source is transmitted through the solar simulator filter.

In circumstances where the irradiance spectrum of the transmitted light does not closely match with the solar irradiance spectrum, structural features of the solar simulator filter, e.g. the thickness of the oxide materials, the thickness of the flexible substrate, the stacking configuration in a multi-layered solar simulator filter, the amount of fluorine or tin in the FTO, and/or the amount of indium or tin in the ITO, may be altered such that the irradiance spectrum of the transmitted light closely matches with the solar irradiance spectrum.

For example, in one embodiment, a maximum irradiance of the transmitted light, which is initially at around 1.8 $W/m^2/nm$ at a wavelength of about 540 nm, may be reduced by at least 5%, preferably at least 10%, but no more than 20%, when the thickness of the flexible substrate is increased by no more than 20%, preferably no more than 40%, relative to an initial thickness of the flexible substrate.

The term "closely matches" as used in this disclosure refers to the circumstances where the difference between two quantities of the same type is no more than +/−20%, preferably no more than +/−10%. For example, the phrase "the irradiance spectrum of the transmitted light closely matches with the solar irradiance spectrum" as used in this disclosure refers to the embodiments where at any given wavelength in the range of 300 to 2,500, the irradiance spectrum of the transmitted light is no more than +/−20%, preferably no more than +/−10% of the value of the solar irradiance at that wavelength. For example, in one embodiment, the value of the solar irradiance at a wavelength of 1000 nm is in the range of 0.76 to 0.79 $W/m^2/nm$, and the irradiance transmitted by the solar simulator filter is approximately 0.8 to 0.82 $W/m^2/nm$, which is no more than +/−10% of the value of the solar irradiance at the wavelength of 1000 nm. A generic solar irradiance spectrum is shown in FIG. 3.

Preferably, the solar simulator filter 100 may be rated as a "Class A" solar simulator filter, in accordance with the IEC 60904-9 or ASTM E927-10 standard. In view of that, when the solar simulator filter is exposed to light provided by one or more light sources and in air mass coefficients of AM1, AM1.5D, or AM1.5G, the transmitted irradiance spectrum at a wavelength range of 300 to 2,500 nm closely matches the solar irradiance spectrum.

According to a third aspect, the present disclosure relates to a method of fabricating the solar simulator filter. The method involves mixing a fluorine-containing compound with water and a first amount of a dihydroxyalkane to form a fluorine-containing solution. Preferably, the fluorine-containing compound may be an ammonium fluoride or a fluoride compound of an alkali metal or an alkaline earth metal. For example, in one embodiment, the fluorine-containing compound is a compound selected from the group consisting of sodium fluoride, lithium fluoride, and potassium fluoride. A concentration of the fluorine-containing compound in the fluorine-containing solution is preferably from 0.01 to about 2.5 mol/L, more preferably from 0.05 to about 1 mol/L. Water is also preferably deionized distilled water. In a preferred embodiment, the dihydroxyalkane is ethylene glycol, and the first amount of the dihydroxyalkane brings a concentration of hydroxyl groups in the fluorine-containing solution of up to 1 mol/L, preferably up to 2 mol/L, but no more than 4 mol/L. Alternative dihydroxyalkanes that may be utilized here include, but are not limited to, dihydroxypropane, dihydroxybutane, dihydroxypentane, dihydroxyhexane, etc.

The method further involves mixing a tin-containing compound with water and a second amount of the dihydroxyalkane to form a tin-containing solution. Preferably, in one embodiment, the tin-containing compound is a tin nitrate, a tin acetate, a tin sulfate, or a hydrate thereof, wherein a concentration of the tin-containing compound in the tin-containing solution is in the range of from about 0.01 to about 2.5 mol/L, or preferably from about 0.05 to about 1 mol/L. In a preferred embodiment, the tin-containing compound is a tin acetate, wherein a concentration of the tin acetate in the tin-containing solution is in the range of from about 0.01 to about 2.5 mol/L, or preferably from about 0.05 to about 1 mol/L. The tin present in the tin-containing compound, i.e. the tin nitrate, the tin acetate, the tin sulfate, or the hydrate thereof, may be $Sn^{2+}$ or $Sn^{4+}$. Preferably, the dihydroxyalkane is ethylene glycol, and the second amount of the dihydroxyalkane brings a concentration of hydroxyl groups in the tin-containing solution of up to 1 mol/L, preferably up to 2 mol/L, but no more than 4 mol/L.

In the next step, the fluorine-containing solution is mixed with the tin-containing solution to form a spin-coating precursor. Preferably, a volume ratio of the fluorine-containing solution to that of the tin-containing solution may be in the range of 1:3 to 1:20, preferably 1:5 to 1:10, preferably about 1:8. In addition, an alkanolamine is added to the spin-coating precursor to adjust a pH of the spin-coating precursor to be in the range of 2 to 6, preferably 3 to 5, more preferably about 3.6. The alkanolamine may be in a protonated form.

In a preferred embodiment, the alkanolamine is triethanolamine. In addition to the alkanolamine, a protonated form of an inorganic acid, e.g. hydrochloric acid or sulfuric acid, may also be utilized to adjust the pH within the range of 2 to 6, preferably 3 to 5, more preferably about 3.6.

Alternative alkanolamines that may be utilized include, but are not limited to, methanolamine, ethanolamine, propanolamine, heptaminol, isoetarine, dimethylethanolamine, and methylaminoethanol.

In an alternative embodiment, the spin-coating precursor is produced by mixing a tin fluoride solution with the alkanolamine, wherein the tin fluoride solution has a concentration of tin fluoride in the range of from about 0.01 to about 2.5 mol/L, preferably from about 0.05 to about 1 mol/L. Furthermore, a molar ratio of hydroxyl groups present in the spin-coating precursor per mole of tin fluoride is in the range of 0.1 to 5, preferably 0.5 to 4. The tin fluoride solution may be produced by mixing a tin fluoride compound with water. The tin present in the tin fluoride compound may be a di-valent tin or a tetra-valent tin.

In one embodiment, the spin-coating precursor is stirred at a temperature in the range of 20 to 100° C., preferably 30 to 95° C., preferably 40 to 90° C., for at least 1 hour, preferably at least 2 hours, but no more than 3 hours. In another embodiment, the spin-coating precursor is stirred at a temperature in the range of 20 to 100° C., preferably 30 to 95° C., preferably 40 to 90° C., until a viscosity of the spin-coating precursor gets a value in the range of 1.5 to 5 cP, preferably 2 to 4 cP, preferably 2.5 to 3 cP, at room temperature (i.e. a temperature in the range of 20 to 30° C., preferably 24 to 26° C., preferably about 25° C.).

In a preferred embodiment, the spin-coating precursor is spin-coated on the flexible substrate to form the solar simulator filter. In view of that, a few droplets of the spin-coating precursor are poured on the flexible substrate, and the flexible substrate is rotated with a centrifugal speed of 2,400 to 3,600 rpm, preferably 2,700 to 3,300 rpm, more preferably about 3,000 rpm, for a period of 10 to 60 seconds, preferably 20 to 50 seconds, more preferably about 30 seconds. Rotating the flexible substrate and the spin-coating precursor may form a layer of the FTO with a thickness in the range of 50 to 200 nm, preferably 100 to 160 nm, preferably 130 to 150 nm. The spin-coating is preferably conducted in an inert atmosphere, i.e. in the presence of an inert gas such as argon, helium, and/or nitrogen, and at a room temperature (i.e. a temperature in the range of 20 to 30° C., preferably 24 to 26° C., preferably about 25° C.). In one embodiment, the solar simulator filter is dried at a temperature in the range of 40 to 80° C., preferably 45 to 70° C., preferably about 50° C., for at least 6 hours, preferably at least 10 hours, but no more than 18 hours.

In one embodiment, the flexible substrate may be formed by dissolving a thermoplastic polymer selected from the group consisting of polyethylene terephthalate, polyethylene, polypropylene, and polyvinyl chloride in an organo-fluorine compound, e.g. trifluoroacetic acid, to form a solution, followed by casting said solution in a mold and drying to form the flexible substrate.

In one embodiment, the method further involves mixing an indium-containing compound with water and a third amount of the dihydroxyalkane to form an indium-containing solution, wherein a concentration of the indium-containing compound in the indium-containing solution is in the range of from about 0.01 to about 2.5 mol/L, or preferably from about 0.05 to about 1 mol/L. In one embodiment, and the indium-containing compound is indium nitrate, indium acetate, indium sulfate, or a hydrate thereof. Preferably, the indium-containing compound is indium (III) nitrate trihydrate. Preferably, the dihydroxyalkane is ethylene glycol, and the third amount of the dihydroxyalkane brings a concentration of hydroxyl groups in the indium-containing solution of up to 1 mol/L, preferably up to 2 mol/L, but no more than 4 mol/L.

In another embodiment, in order to produce a multi-layered solar simulator filter, a few droplets of the spin-coating precursor (that include the FTO and/or the ITO) are poured on said dried solar simulator filter and the spin-coating and the drying steps are repeated until a desired stacking configuration and a desired total thickness is obtained for the multi-layered solar simulator filter.

The FTO and/or the ITO may be disposed on the flexible substrate using other techniques known in the art, such as plasma-enhanced sputtering, ion plate coating, physical vapor deposition, magnetron sputtering, ion beam sputtering, ion-assisted electron beam deposition, and the like.

The examples below are intended to further illustrate protocols for the solar simulator filter and the method of fabricating thereof, and are not intended to limit the scope of the claims.

Example 1

The chemicals used in various embodiments of the present invention were supplied by Aldrich Company as analytical grade reagents. The raw materials were used as purchased without further purification.

The polyethylene terephthalate solution was dissolved in trifluoroacetic acid (TFA) as a solvent. The obtained solution was prepared via casting the solution on a cuboid glass mold to obtain solid layer.

The precursors of ITO layer indium nitrate trihydrate, i.e. $In(NO_3)_3.3H_2O$, and tin acetate, i.e. $Sn(CH_3COO)_4$, and ethylene glycol. The solutions of indium oxide and tin oxide was separately prepared by dissolving $In(NO_3)_3.3H_2O$ and $Sn(CH_3COO)_4$ in ethylene glycol. Two solutions were mixed and stirred for 2 h. After 2 h, the nominal value of triethanolamine (TEA) was added to the mixed solution to obtain pH of 3.6. ITO film was coated on PTE with spinning parameters of 3000 rpm and 30 s and dried at 50° C.

A solar simulator filter was formed using a polymer substrate and conducting metal oxide film layer. A conducting metal oxide layer was deposited on the flexible polymer substrate by sputtering system. The transmission of the filter was measured using a UV/Vis spectrophotometer.

FIG. 2 shows a transmission spectrum of the solar simulator filter with a layer of the ITO disposed onto the flexible substrate.

The maximum transparency at 540 was about 80%. After 540 nm, the transmission of the filter is decreased with increasing wavelength.

FIG. 3 shows the irradiance spectrum of the solar simulator filter compared to the solar irradiance spectrum. As shown in FIG. 3, the irradiance spectrum provided by the solar simulator filter very well matched with the solar irradiance spectrum ranging from 300 nm to 2,500 nm.

The invention claimed is:

1. A solar simulator filter, comprising:
   a flexible substrate; and
   an oxide material, wherein the oxide material comprises fluorine-doped tin oxide in the form of a layer disposed on the flexible substrate, and indium-doped tin oxide in the form of a layer disposed on the fluorine-doped tin oxide,
   wherein an amount of fluorine in the fluorine-doped tin oxide is in the range of 0.1 to 5 wt %, relative to the total weight of the fluorine-doped tin oxide,
   wherein an amount of indium in the indium-doped tin oxide is in the range of 8 to 10 wt %, relative to the total weight of the indium-doped tin oxide,
   wherein the layer of fluorine-doped tin oxide and the layer of indium-doped tin oxide each independently have a thickness in a range of 50-200 nm,
   wherein the solar simulator filter transmits light having an irradiance in the range of 1.0 to 1.6 $W/m^2/nm$ in the wavelength range of 300 to 750 nm, an irradiance in the range of 0.4 to 1.0 $W/m^2/nm$ in the wavelength range of 750 to 1,400 nm, and an irradiance in the range of 0.1 to 0.4 $W/m^2/nm$ in the wavelength range of 1,400 to 2,500 nm,
   wherein the flexible substrate has a thickness in the range of 50 μm to 5 mm, and
   wherein the flexible substrate has a flexural modulus in the range of 1 to 50 MPa and a flexural strength in the range of 0.5 to 20 MPa.

2. The solar simulator filter of claim 1, wherein the flexible substrate has a transmittance of at least 60% at a wavelength in the range of 300 to 2,500 nm.

3. The solar simulator filter of claim 1, wherein the flexible substrate is a thermoplastic polymer selected from the group consisting of polyethylene terephthalate, polyethylene, polypropylene, and polyvinyl chloride.

4. The solar simulator filter of claim 3, wherein the flexible substrate is polyethylene terephthalate.

5. The solar simulator filter of claim 1, wherein an average particle size of the fluorine-doped tin oxide is in the range of 1 to 100 nm.

6. The solar simulator filter of claim 1, which has a surface resistivity in the range of 5 to 60 Ω/sq.

7. A solar simulator device, comprising:
   at least one light source with a power output in the range of 0.1 to 1.5 $W/m^2/nm$; and
   the solar simulator filter of claim 1 disposed within a distance of 0.1 to 5 m from said light source,
   wherein at least a portion of light provided by said light source is configured to transmit through the solar simulator filter.

8. The solar simulator filter of claim 1, further comprising a second layer of fluorine-doped tin oxide disposed on the layer of indium-doped tin oxide.

9. The solar simulator filter of claim 8, wherein the second layer of fluorine-doped tin oxide has a thickness in a range of 50-200 nm.

10. The solar simulator filter of claim 1, which has a thickness in a range of 3-5 mm.

\* \* \* \* \*